United States Patent [19]

Franzen, Jr.

[11] Patent Number: 5,482,355
[45] Date of Patent: Jan. 9, 1996

[54] ORTHOPEDIC PILLOW

[76] Inventor: Paul W. Franzen, Jr., 550 Ridge Pike, Lafayette Hill, Pa. 19444

[21] Appl. No.: 44,951

[22] Filed: Apr. 9, 1993

[51] Int. Cl.[6] .............................. A47C 7/40; A47C 7/38
[52] U.S. Cl. ................... 297/410; 297/391; 297/452.33; 297/284.1; 606/240
[58] Field of Search ............................. 297/284.1, 284.3, 297/391, 396, 410, 452.29, 452.33; 5/630, 633, 652; 128/870; 606/240–242

[56] References Cited

U.S. PATENT DOCUMENTS

| | | |
|---|---|---|
| D. 272,300 | 1/1984 | Dziurman, Jr. . |
| 587,224 | 7/1897 | McKelvey . |
| 1,746,080 | 2/1930 | Hamilton ............................ 606/240 X |
| 2,521,780 | 9/1950 | Dodd . |
| 2,869,621 | 1/1959 | Zukor . |
| 2,896,227 | 7/1959 | Reed . |
| 3,340,969 | 9/1967 | Rothberg . |
| 3,578,383 | 5/1971 | Earl . |
| 3,608,965 | 9/1971 | Cziptschirach . |
| 3,642,321 | 2/1972 | Schwarz, II . |
| 3,825,301 | 7/1974 | Schwarz, II . |
| 4,285,081 | 8/1981 | Price . |
| 4,424,599 | 1/1984 | Hannouche . |
| 4,754,513 | 7/1988 | Rinz . |
| 4,756,551 | 7/1988 | Miller . |
| 4,796,953 | 1/1989 | Pereira . |
| 4,805,603 | 2/1989 | Cumberland . |
| 4,821,355 | 4/1989 | Burkhardt . |
| 4,824,169 | 4/1989 | Jarrell .................................... 297/284.1 |
| 4,829,614 | 5/1989 | Harper . |
| 4,838,611 | 6/1989 | Talaugon . |
| 4,862,536 | 9/1989 | Pruit . |
| 5,070,865 | 12/1991 | Iams ......................................... 606/240 |
| 5,201,761 | 4/1993 | Serola ..................................... 5/633 X |

FOREIGN PATENT DOCUMENTS 2178652  2/1987  United Kingdom .............. 297/452.29

*Primary Examiner*—Peter R. Brown
*Attorney, Agent, or Firm*—John F. A. Earley; John F. A. Earley, III

[57] ABSTRACT

An orthopedic pillow for helping to correct and helping to prevent hyperkyphosis and rigidity of the thoracic spine and for returning the normal lordotic cervical curve comprises a base panel having a first end portion, a second end portion, a left top surface segment extending between the first end portion and the second end portion, and a right top surface segment extending between the first end portion and the second end portion, a first crown for supporting the thoracic spine, the first crown being formed on the first end portion of the base panel, extending toward the second end portion of the base panel, and dividing at least partially the left top surface segment from the right top surface segment, and a transition ramp formed in the first end portion of the first crown for supporting the spine just under and below the shoulder blades of a reclining person. Other embodiments of the invention include a cylindrical pillow having a transition ramp, a removable pillow apparatus for supporting the neck of a person sitting in a bucket seat of a car, and a chair having a pillow having a substantially semi-cylindrical shape with a center axis that extends between its upper end portion and its lower end portion.

3 Claims, 6 Drawing Sheets

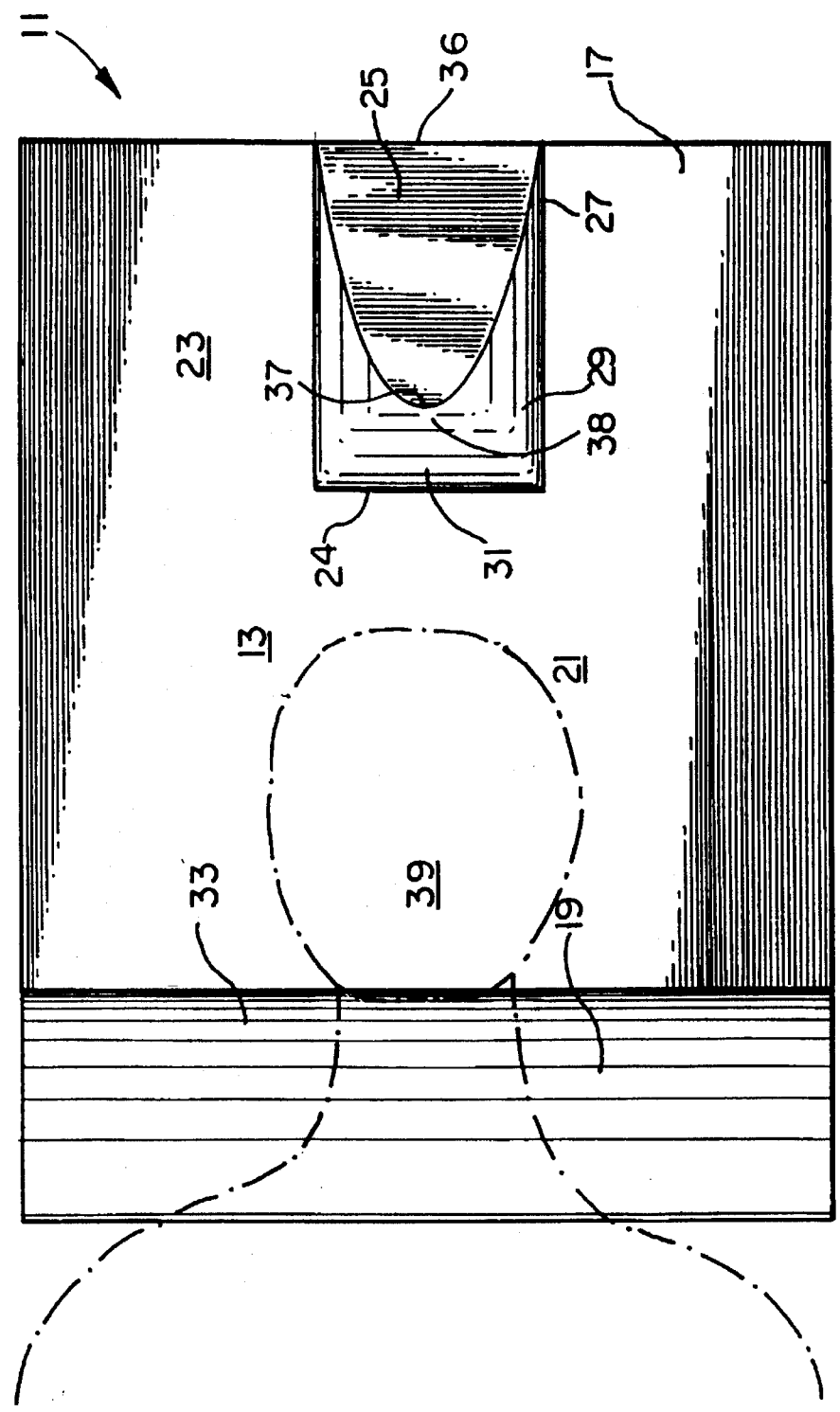

5,482,355

ORTHOPEDIC PILLOW

BACKGROUND OF THE INVENTION

1. Field of the Invention

The present invention relates to the field of orthopedic devices for the back, and more particularly concerns an orthopedic pillow for helping to correct and helping to prevent hyperkyphosis and rigidity of the thoracic spine and for returning the normal lordotic cervical curve.

2. Description of the Prior Art

Conventional orthopedic pillows comprise a base panel having a first end portion, a second end portion, and a top surface, and a crown formed on the top surface extending along the length of the first end portion of the base panel. Such an orthopedic pillow is designed to support the neck area of a person reclining on the pillow, the crown resting against the neck area of the person lying on the pillow.

However, this pillow does not adequately attend to the problem of hyperkyphosis and rigidity of the thoracic spine.

Hyperkyphosis of the dorsal curve usually starts with the loss of the cervical curve, that is, a flattening out or a reversal in shape of the cervical spine, a condition that existing orthopedic pillows try to correct. Loss of the cervical curve causes the remaining three interconnecting curves of the spinal column to adjust to maintain the body's center of gravity. Therefore, the hyperkyphotic curve of the dorsal spine, which is next to the cervical curve, also must be corrected to correct hyperkyphosis. If the hyperkyphotic curve is not corrected, but the cervical curve is corrected, a gooseneck type of cervical curve is developed rather than the normal 35-45 degree curves of both the cervical and thoracic spines. Existing orthopedic pillows do not address the problems relating to the hyperkyphotic curve.

SUMMARY OF THE INVENTION

It is an object of the invention to provide an orthopedic pillow for correcting hyperkyphosis and rigidity of the thoracic spine and for returning the normal lordotic cervical curve.

Another object of the invention is to provide an orthopedic pillow which promotes good posture.

Still another object of the invention is to provide an orthopedic pillow that may be used to support the neck area of a reclining person and that may be used to promote correction of hyperkyphosis and rigidity of the thoracic spine.

Another object of the invention is to provide a removable pillow apparatus for supporting the head of a person sitting in a bucket seat of a car, said pillow promoting proper posture.

Still another object of the invention is to provide a chair having an orthopedic pillow for supporting the neck area of a person sitting in the chair and for promoting correct alignment of the thoracic spine of the person sitting in the chair.

BRIEF DESCRIPTION OF THE DRAWINGS

FIG. 1b is a view in top plan of an orthopedic pillow constructed in accordance with this invention;

DETAILED DESCRIPTION

Figure 1A:
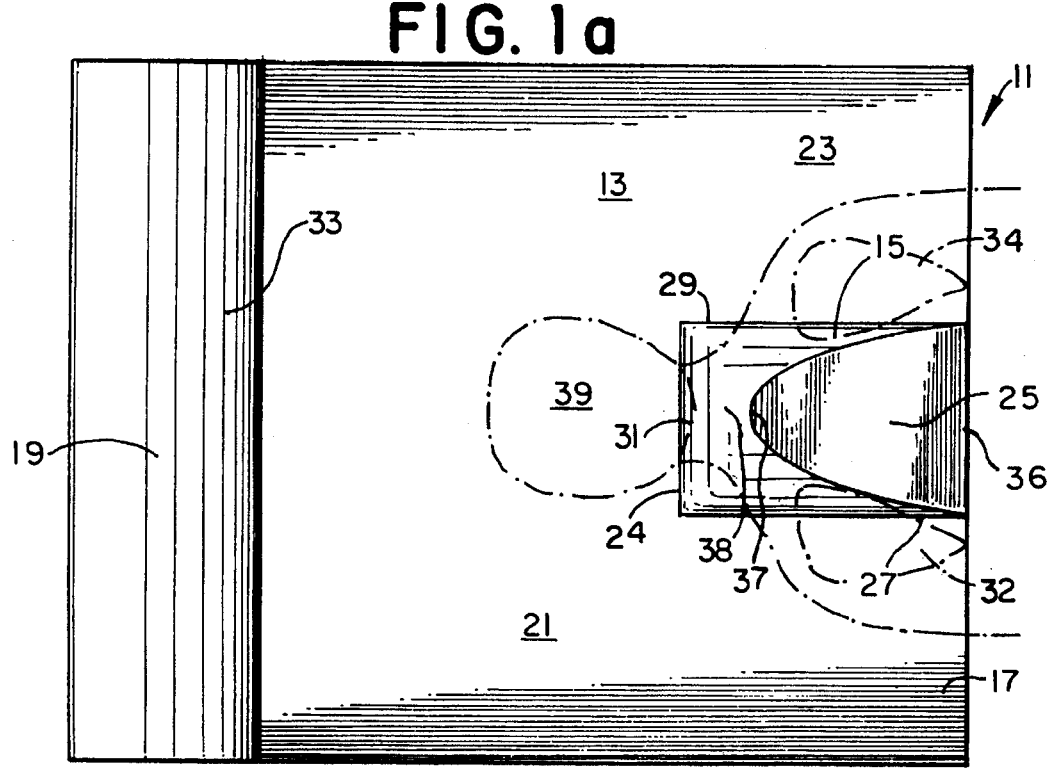
FIG. 1a is a view in top plan of an orthopedic pillow/ constructed in accordance with this invention.
Figure 2:
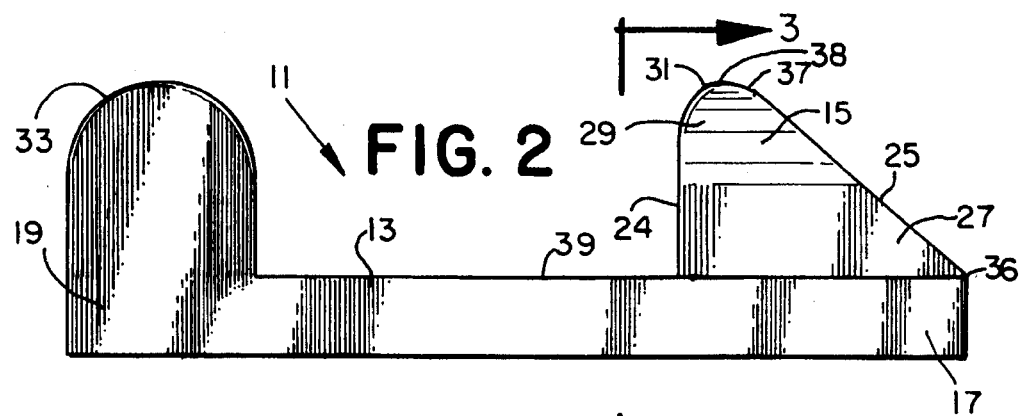
FIG. 2 is a view in side elevation of the orthopedic pillow of FIGS. 1a and 1b.
Figure 3:
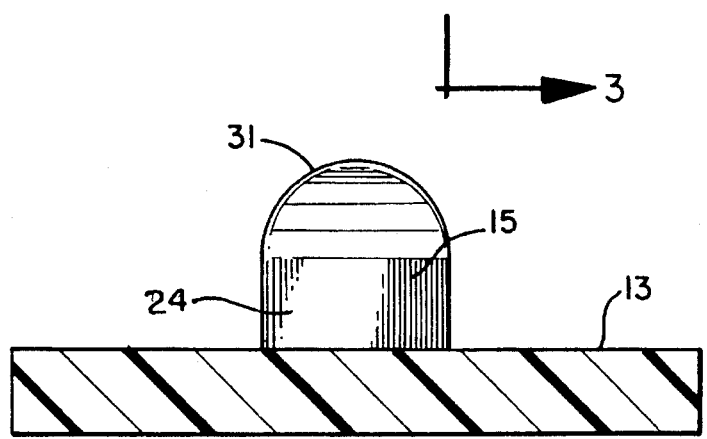
FIG. 3 is a view in cross section taken along the lines and arrows 3—3 of FIG. 2.

Turning to the drawings, there is shown in FIGS. 1–3 an orthopedic pillow 11 for correcting hyperkyphosis and rigidity of the thoracic spine and for returning the normal lordotic cervical curve which comprises a base panel 13 and a first crown 15 formed on the base panel 13 for supporting the thoracic spine.

Base panel 13 has a first end portion 17 and a second end portion 19. Looking onto base panel 13 from the first end portion 17 towards the second end portion 19, there is a left top surface segment 21 that extends between first end portion 17 of base panel 13 and second end portion 19 of base panel 13. Similarly, a right top surface segment 23 extends between first end portion 17 of base panel 13 and second end portion 19 of base panel 13.

First crown 15 is formed on the first end portion 17 of base panel 13 and extends towards the second end portion 19 of base panel 13, ending at end portion 24 and partially dividing the left top surface segment 21 from the right top surface segment 23.

A transition ramp 25 is formed in the first end portion 27 of the first crown 15, and transition ramp 25 slopes upwardly in a direction from the first end portion 27 of crown 15 toward the second end portion 29 of first crown 15. That is, ramp 25 slopes upwardly from its lower end portion 36 to its upper end portion 37. Preferably, the transition ramp 25 slopes at an angle between 35 degrees and 45 degrees, and more preferably slopes at an angle of about 40 degrees.

A beveled portion 31 is formed in the second end portion 29 of first crown 15 for supporting the neck area of a reclining person. The beveled portion 31 slopes downwardly in a direction from the first end portion 27 of crown 15 towards the second end portion 29 of first crown 15.

A portion 38 in crown 15 between beveled portion 31 and the upper end 37 of ramp 25 supports the neck area of the user, as is explained below.

Preferably, the ratio of the length of the ramp section of the crown 15 to the length of the remainder of the crown 15 (the neck support section of the crown) ranges from 3/1 to 5/2. That is, the ratio for the distance between a first plane that is normal to the top surfaces 21 and 23 and that extends along the lower end portion 36 of ramp 25 and a second plane that is parallel to the first plain and that extends through the upper end portion 37 of ramp 25 and the distance between the second plane and a third plane that is parallel to the first and second planes and that extends along the end portion 24 of first crown 15 ranges between 3/1 and 5/2.

A second crown 33 is formed on the second end portion 19 of base panel 13, and second crown 33 extends across base panel 13 perpendicularly to the longitudinal axis of the first crown 15 for supporting the neck area of a reclining person, as illustrated in FIG. 1b.

Pillow 11 is made from an inflatable material such as plastic. However, pillow 11 may be made from foam rubber material such as one or two pound foam made by Reilly Foam Co., Conshohocken, Pa., and, similarly to the pillow shown in FIG. 9, base panel 13 may include a wooden or fiberglass support sheet.

In use, pillow 11 is placed on a flat surface such as a bed. The user of the pillow, as shown in FIG. 1a, reclines with his back facing down onto pillow 11 such that first crown 15 lies between his shoulder blades 32 and 34. The lower end portion 36 of transition ramp 25 is positioned at the dorsal or thoracic vertebrae 6 or 7, that is, just below the user's shoulder blades 32 and 34, and upper end portion 37 of transition ramp 25 is positioned at the dorsal or thoracic vertebrae 1. Accordingly, ramp 25 supports the user's spine between the dorsal or thoracic vertebrae 6 or 7 and the dorsal or thoracic vertebrae 1.

The user's head rests on central area 39 of base panel 13, and beveled portion 31 rests against the bottom of the user's skull. The portion 38 between beveled portion 31 and the upper end 37 of ramp 25 supports; the neck area of the user.

If the user wishes only to have the his neck supported, pillow 11 is rotated 180 degrees so that the user's head lies on central area 39 and the user's neck lies on and is supported by second crown 33, a horizontal cylinder, as shown in FIG. 1b.

Figure 4:
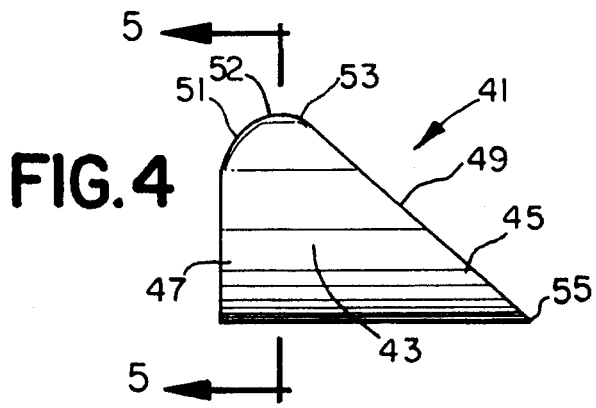
FIG. 4 is a view in side elevation of an alternative embodiment of the invention.
Figure 5:
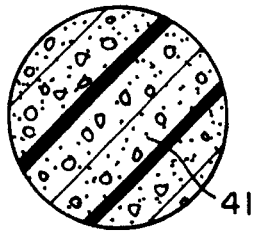
FIG. 5 is a view in cross section taken along the lines and arrows 5—5 of FIG. 4.

Referring to FIGS. 4 and 5, an alternative embodiment of the invention is shown. In this embodiment, orthopedic pillow 41 comprises a cylindrical body 43 having a first end portion 45 and a second end portion 47. A transition ramp 49 is formed in the first end portion 45 and slopes upwardly in a direction from the first end portion 45 of body 43 toward the second end portion 47 of body 43.

The transition ramp 49 preferably slopes at an angle between 35 degrees and 45 degrees, and more preferably slopes at an angle of about 40 degrees.

A beveled portion 51 is formed on the second end portion 47 of body 43, and beveled portion 51 slopes downwardly in a direction from the first end portion 45 of body 43 towards the second end portion 47 of body 43. A portion 52 is disposed between the beveled portion 51 and the upper end portion 53 of the transition ramp 49 for supporting the neck area of the user of pillow 41.

Like crown 15 of pillow 11, the ratio of the ramp section of body 43 to the length of the remainder of body 43 (the neck support section) preferably ranges from 3/1 to 5/2.

Pillow 41 is preferably made of a foam rubber material, such as one or two pound foam made by Reilly Foam Co.

Pillow 41 is used in substantially the same way as first crown 25 of pillow 11. Pillow 41 is positioned between the shoulder blades of someone lying on his back, with the lower end portion 55 of transition ramp 49 positioned at the dorsal or thoracic vertebrae 6 or 7, that is, just below shoulder blades of the user. Upper end portion 53 of transition ramp 49 is positioned at the dorsal or thoracic vertebrae 1. Accordingly, ramp 49 supports the users's spine between the dorsal or thoracic vertebrae 6 or 7 and the dorsal or thoracic vertebrae 1. Beveled portion 51 rests against the bottom of the user's skull, and portion 52 between beveled portion 51 and upper end portion 53 of transition ramp 49 supports the neck area of the user.

Figure 6:
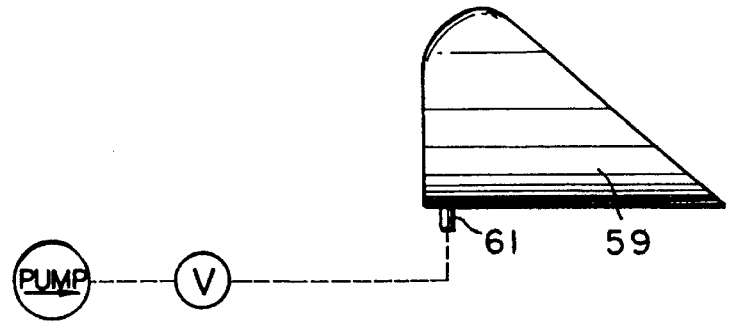
FIG. 6 is a view in side elevation of another alternative embodiment of the invention.

Referring to FIG. 6, another alternative embodiment of the invention is shown. Here, pillow 59 is substantially the same as pillow 41, except pillow 59 is made of an inflatable plastic or rubber material, such as the material of the inflatable rubber bladder made by Monarch, rather than of the foam rubber material of pillow 41. Pillow 59 is shown inflated in FIG. 6. Pillow 59 is provided with an inflation valve 61 through which air is passed to inflate pillow 59.

Pillow 59, after being inflated, is used in the same fashion as pillow 41.

Figure 7:
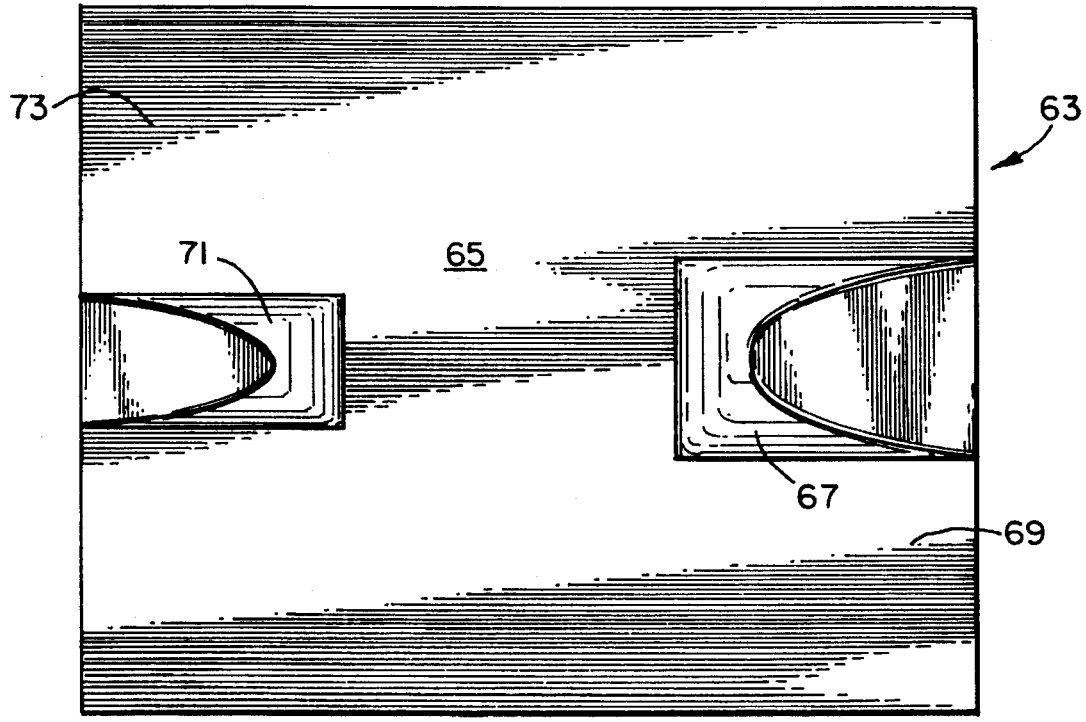
FIG. 7 is a view in top plan of another alternative embodiment of the invention.

FIG. 7 shows another alternative embodiment of the invention which comprises an orthopedic pillow 63 for correcting hyperkyphosis and rigidity of the thoracic spine and for returning the normal lordotic curve. Pillow 63 comprises a base panel 65, a first crown 67 formed on the first end portion 69 of base panel 65, and a second crown 71 formed on the second end portion 73 of base panel 65.

The configurations of first crown 67 and second crown 71 are substantially the same as the configuration of first crown 15 shown in FIGS. 1–3. First crown 67 is larger than second crown 71 to permit pillow 63 to be used by a small person or a large person, the small person using second crown 71 between his shoulder blades and the large person using first crown 67 between his shoulder blades. Also, a patient may start with the smaller second crown 71, and then, as the patient's physical condition improves, or as the patient grows if the patient is a child or teenager, proceed to using larger first crown 67.

Like crown 15 of pillow 11, the ratio of the length of the ramp sections of crowns 67 and 71 to the length of the remainder of crowns 67 and 71 (the neck support sections) preferably ranges from 3/1 to 5/2.

Pillow 63 may be inflatable, like pillow 11, or pillow 63 may be made of foam rubber material which is optionally supported by a wooden or fiberglass sheet.

Figure 8:
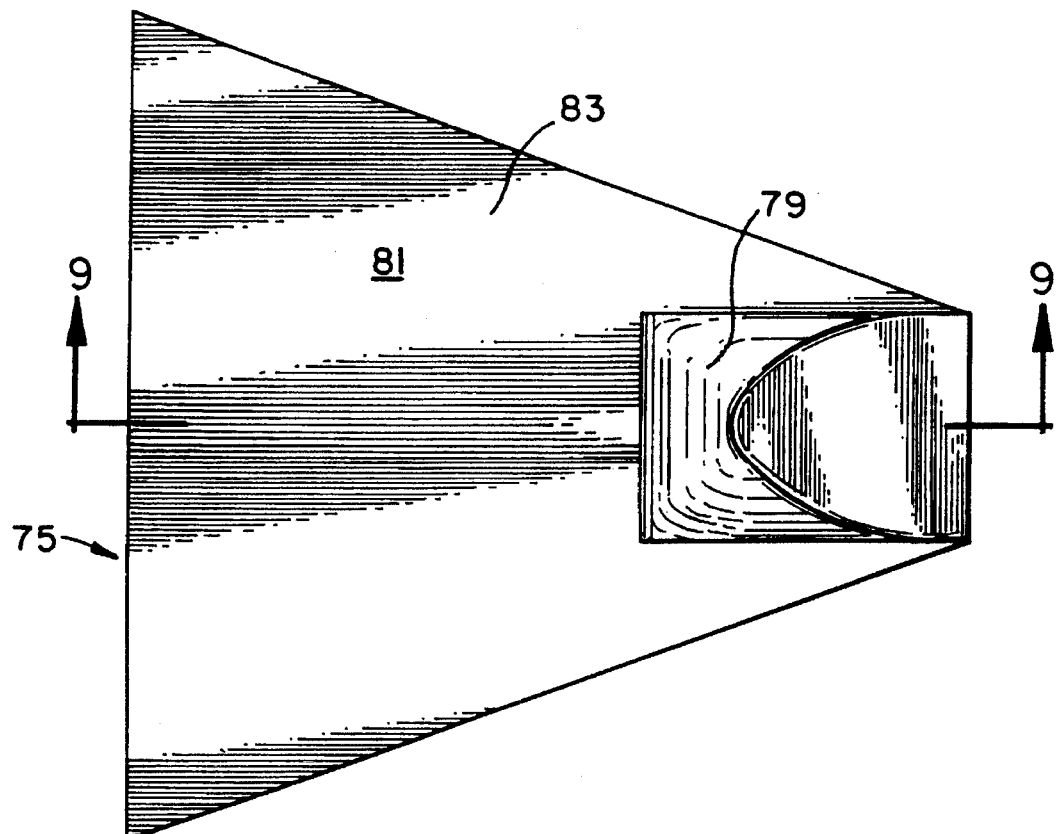
FIG. 8 is a view in top plan of another alternative embodiment of the invention.
Figure 9:
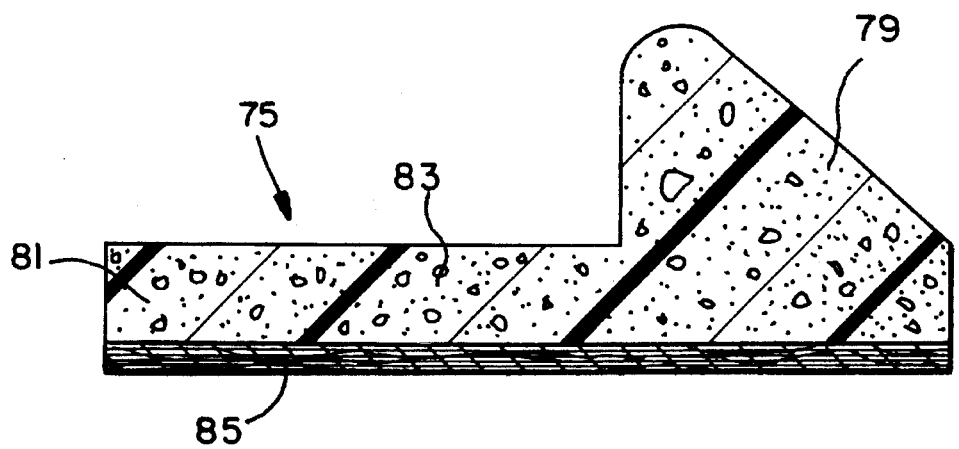
FIG. 9 is a view in cross section taken along the lines and arrows 9—9 of FIG. 8.

FIGS. 8 and 9 show another alternative embodiment of the invention. Here, there is shown an orthopedic pillow 75 for a child. Crown 79 has a configuration substantially the same as first crown 15 shown in FIGS. 1–3. Base panel 81 has a substantially trapezoidal-shaped top surface to facilitate use of the pillow 75 by child. Because the base panel 81 is tapered inwardly near crown 79, the base panel 81 does not support the child's back around the child's shoulder blades, thereby permitting gravity to pull the child's shoulders downwardly around crown 79 and encouraging the stretching-out of the pectoral muscles. In addition to promoting correction of hyperkyphosis, use of the pillow 75 teaches a child to stand up straight, something that is not instinctive and must be learned. Also, pillow 75 is useful in the treatment of children having rounded shoulders.

Like crown 15 of pillow 11, the ratio of the length of the ramp section of the crown 79 of pillow 75 to the length of the remainder of the crown 79 (the neck support section) preferably ranges from 3/1 to 5/2.

As shown in FIG. 9, crown 79 and the upper portion 83 of base panel 81 are made of a foam rubber material, such as one or two pound foam made by Reilly Foam Co., and the lower portion 85 of base panel 81 comprises a sheet of wood or fiberglass affixed to upper portion 83 of base panel 81.

Alternatively, pillow 75 may be made of an inflatable plastic material.

Figure 10:
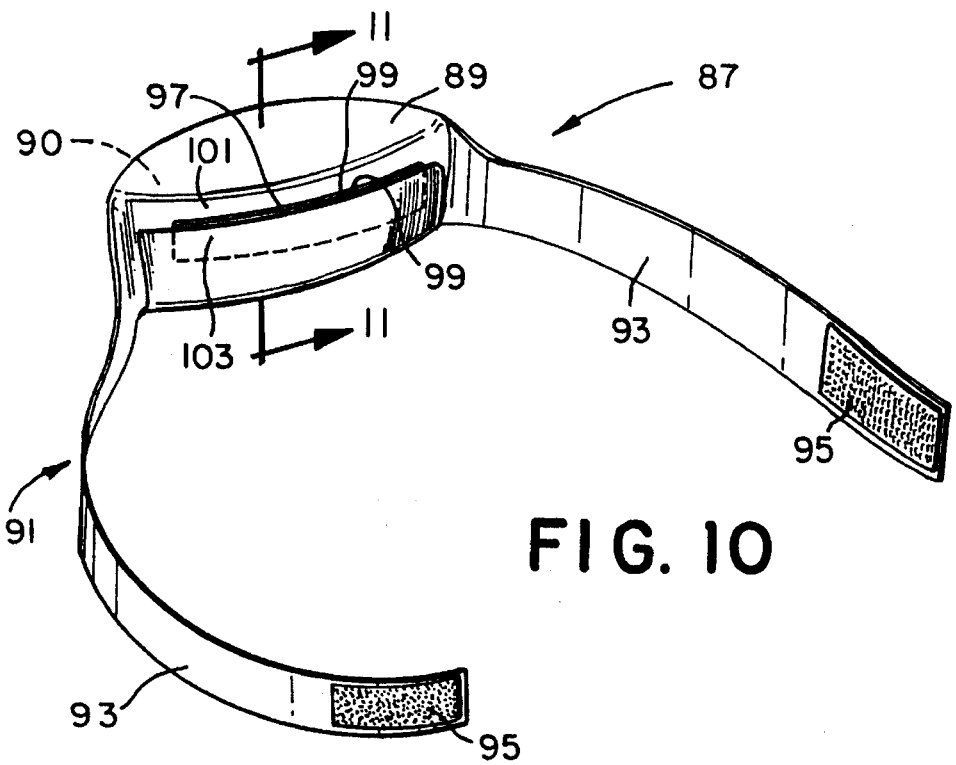
FIG. 10 is a view in perspective of a removable pillow apparatus constructed in accordance with the invention.
Figure 11:
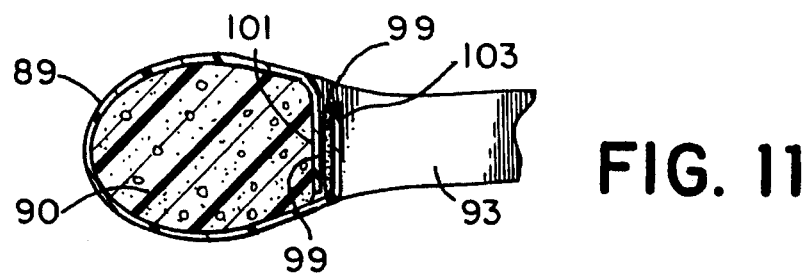
FIG. 11 is a view in cross section taken along the lines and arrows 11—11 of FIG. 10.

FIGS. 10 and 11 show still another alternative embodiment of the invention. Here, there is shown a removable pillow apparatus 87 for supporting the head of a person sitting in a bucket seat of a car. Pillow apparatus 87 comprises a pouch 89 for receiving the back of a person's neck, a pillow 90 housed inside pouch 89, and means 91 for adjustably securing the pouch 89 at a desired location on a car seat and for permitting removal of the pouch from the car seat when desired.

Attachment means 91, as shown in FIG. 10, includes a pair of straps 93 extending from pouch 89, and velcro attachment members 95 secured to the ends of straps 93.

Pouch 89 is provided with an opening 97 to permit pillow 90 to be removed when it is desired to launder pouch 89 and straps 93.

Velcro attachment members 99 are secured along opposed panels 101 and 103 which form opening 97 for closing opening 97 to secure pillow 90 inside the pouch 89.

In use, pillow 90 is inserted through opening 97 into pouch 89, and velcro attachment members 99 are pushed into contact with each other to close opening 97 to secure pillow 90 inside pouch 89. Pillow apparatus 87 is then placed on the bucket seat of a car by wrapping straps 93 around the car seat and securing the ends of the straps 93 together with velcro attachment members 95. The pillow apparatus 87 is positioned on the car seat such that the back of the neck of the person sitting in the car seat rests against pouch 89.

Because pillow apparatus 87 may be secured at any height on the back of the car seat using adjustment means 91, pillow apparatus 87 may be used by short people, people of medium height, and tall people.

Figure 12:
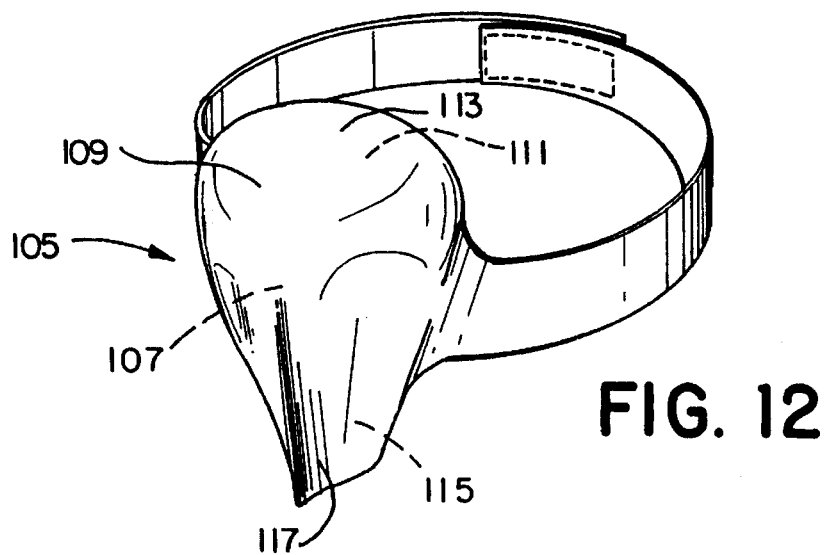
FIG. 12 is a view in perspective of an alternative embodiment of the removable pillow apparatus constructed in accordance with the invention.

FIG. 12 shows another pillow apparatus 105. Pillow apparatus 105 is substantially the same as pillow apparatus 87, except pillow 107 and pouch 109 have a semi-conical shape. The semi-conical shape promotes correct alignment of a thoracic spine of a person sitting against the pillow apparatus 105 since the pillow apparatus is placed to position the pillow 107 (and pouch 109) between the shoulder blades of the person sitting against pillow apparatus 105.

Like the crown 15 of pillow 11, the ratio of the length of the lower end portions 115, 117 of pillow apparatus 105 to the length of the remainder of the pillow apparatus 105 (the upper end portions 111, 113) preferably ranges from ¾ to ⅝.

Figures 13, 14:
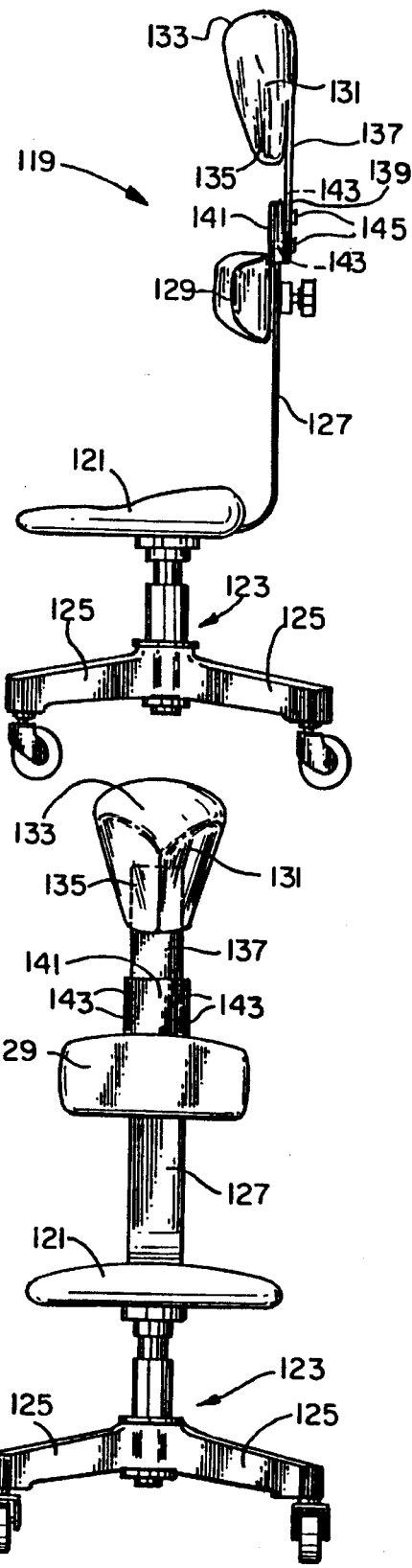
FIG. 13 is a view in side elevation of a chair constructed in accordance with the invention.
FIG. 14 is a view in front elevation of the chair shown in FIG. 13.

FIGS. 13 and 14 show still another alternative embodiment of the invention. Here, a chair 119 is shown having a seat 121, a support member 123, including legs 125, for supporting seat 121 above the floor, and a back support member 127 extending upwardly from seat 121. A first pillow 129 is mounted on back support member 127 using a conventional hand screw device 128 to receive the back of a person sitting in the seat 121. Hand screw drive device 128 comprises a bracket that is attached to pillow 129 by any conventional manner (e.g., bolts, screws, or the like). The bracket wraps, at least partially, around back support member 127 so that the bracket may slide up and down on back support member 127 without disengaging from back support member 127 unless the bracket is slid upwardly beyond the top of back support member 127. The bracket is provided with a threaded bore that extends through the bracket and that is adapted to receive a threaded bolt having a handle mounted on its outer end portion. Pillow 129 may be positioned in any desired position along back support member 127 by (1) sliding the bracket up or down on back support member 127 to position the pillow 129 in the desired position, and, then, (2) screwing the bolt inwardly by turning its handle so that the end of the bolt advances through the threaded bore of the bracket and pushes tightly against the back side of back support member 127. By continuing to screw the bolt inwardly after the bolt contacts the back side of the back support member 127, the wrap-around portion of the bracket, that is, the portion of the bracket on the front side of the back support member 127, is pulled into tight contact with the front side of the back support member 127. The bolt is screwed inwardly until the back support member 127 is tightly squeezed between the wrap-around portion of the bracket in contact with the front side of the back support member 127 and the end of the bolt in contact with the back side of the back support member 127.

The position of the back support member may be repositioned by unscrewing the bolt using its handle to permit the bracket to slide along the back support member 127 again and then retightening the bracket to the back support member 127 in a new position along the back support member 127.

A second pillow 131 is mounted on back support member 127 above first pillow 129 for supporting the neck area of a person sitting on seat 121 and for promoting correct alignment of a thoracic spine of a person sitting on the seat 121.

Second pillow 131 has an upper end portion 133, a lower end portion 135 having a substantially semiconical shape.

Like the crown 15 of pillow 11, the ratio of the length of the lower end portion 135 of pillow 131 to the length of the remainder of the pillow 131 (the upper end portion 133) preferably ranges from ¾ to ⅝.

Second pillow 131 is attached to a bar 137, and a plate 139 is mounted on the lower end portion of bar 137. Using a second plate 141 and screws 143 and nuts 145, the height of second pillow 131 may be adjusted up or down such that the second pillow 131 is positioned between the shoulder blades of the person sitting in the chair by sandwiching the barlike back support member 127 between plates 139 and 141.

In use, after the second pillow 131 is positioned at the appropriate height, the user of the chair sits back against pillow 131 so that the pillow 131 lies between his shoulder blades. The end of the lower end portion 135 is positioned at the dorsal or thoracic vertebrae 6 or 7, that is, just under and between the user's shoulder blades, and upper end portion 133 is positioned at the dorsal or thoracic vertebrae 1. Accordingly, pillow 131 supports the user's spine between the dorsal or thoracic vertebrae 6 or 7 and the dorsal or thoracic vertebrae 1.

The user's head is positioned just above upper end portion 133, with the back his neck resting against the upper end portion 133 of pillow 131.

Alternatively, the back support member 127 may be formed to have a longer length, thereby eliminating the need for an extension bar 137. The length of such a longer length back support member 127 is sufficiently long such that it may receive a first pillow 129 for supporting the back of a person sitting in the seat 121 and a second pillow 131 for supporting the neck area of a person sitting on seat 121 and for promoting correct alignment of the thoracic spine of a person sitting on a seat 121. Further, the length of such a longer length back support member 127 is sufficiently long to accommodate the different heights of various users. First pillow 129 may be adjustably mounted on a lower portion of support member 127 with a conventional hand screw device, as shown in FIG. 13. By loosening the conventional hand screw device by unscrewing it, the first pillow 129 may be moved up or down along the back support member 127 to position it at the correct height for the user of the chair 19. Then, pillow 129 may be fixed in the desired location by tightening the hand screw device. In this embodiment, second pillow 131 is also provided with a conventional hand screw device so that it may be adjusted up or down along the back support member 127 to the desired height in the same manner as pillow 129.

ADVANTAGES

The invention promotes the restoration of the correct curves in the spinal column from the seventh dorsal vertebrae on up.

The invention may be used as a preventive measure against the development of hyperkyphosis since the use of the invention promotes correct posture.

The invention helps to correct the effects of the sedentary life style of the 20th century and the computer age.

Slouching or hyperkyphosis may result in as much as a 30% loss of lung capacity, drowsiness, fatigue, limited range of motion, premature aging, and reduced blood flow to the brain. Correct posture helps avoid these conditions, and the invention promotes correct posture.

By promoting correction of hyperkyphosis, the effects of osteoporosis are not so severe.

Correct posture, which is promoted by the invention, leads to more calories being burned in a person's body.

I claim:

1. A chair comprising a seat, first support means attached to the seat for supporting the seat, second support means mounted on the seat and extending upwardly from the seat for supporting the back of a person sitting on the seat, and third support means mounted on the second support means for supporting the neck area of a person sitting on the seat and for promoting correct alignment of a thoracic spine of a person sitting on the seat, said third support means including a pillow having an upper end portion and a lower end portion, the lower end portion having a substantially semi-conical shape having a generally semi-circular cross-section and being tapered from an upper end of the lower end portion to a lower end of the lower end portion, the upper end of the lower end portion having a width that is greater than a relatively narrow width of the lower end of the lower end portion, and an upright member to which the pillow is attached, the upright member having attachment means for mounting the upright member to the second support means.

2. The chair of claim 1, the attachment means being adjustable to allow for proper positioning of the pillow with respect to the height of the chair's user.

3. The chair of claim 1, the lower end portion of the pillow having a longitudinal length, the upper end portion of the pillow having a longitudinal length, and the ratio of the length of the lower end portion of the pillow to the length of the upper end portion of the pillow ranging from ¾ to ⅝.

* * * * *